United States Patent
Nagarajan et al.

(10) Patent No.: US 11,739,219 B2
(45) Date of Patent: Aug. 29, 2023

(54) BIOLOGICALLY-DERIVED CARBON BLACK ALTERNATIVE AND METHOD OF MAKING THE SAME

(71) Applicant: Living Ink Technologies, LLC, Fort Collins, CO (US)

(72) Inventors: Aparna Nagarajan, Thornton, CO (US); Fiona Davies, Lakewood, CO (US); Scott Fulbright, Denver, CO (US); Stevan Albers, Fort Collins, CO (US); Kangmin Kim, Westminster, CO (US)

(73) Assignee: Living Ink Technologies, LLC, Berthoud, CO (US)

( * ) Notice: Subject to any disclaimer, the term of this patent is extended or adjusted under 35 U.S.C. 154(b) by 98 days.

(21) Appl. No.: 17/315,204

(22) Filed: May 7, 2021

(65) Prior Publication Data

US 2021/0347996 A1   Nov. 11, 2021

Related U.S. Application Data

(60) Provisional application No. 63/021,494, filed on May 7, 2020.

(51) Int. Cl.
| | | |
|---|---|---|
| *C09C 1/48* | (2006.01) | |
| *C12P 3/00* | (2006.01) | |
| *C01B 32/05* | (2017.01) | |

(52) U.S. Cl.
CPC ................ *C09C 1/48* (2013.01); *C01B 32/05* (2017.08); *C12P 3/00* (2013.01); *C01P 2006/60* (2013.01)

(58) Field of Classification Search
CPC .................................. C09C 1/48; C01B 32/05
See application file for complete search history.

(56) References Cited

U.S. PATENT DOCUMENTS

| | | | |
|---|---|---|---|
| 4,284,616 A | 8/1981 | Solbakken et al. | |
| 8,323,793 B2* | 12/2012 | Hamby | ................... C10B 53/07 425/222 |
| 9,758,757 B2* | 9/2017 | Harlin | .................... D21H 17/21 |
| 10,829,613 B2 | 11/2020 | Schwaiger et al. | |
| 2014/0373752 A2 | 12/2014 | Hassinen et al. | |
| 2015/0240093 A1 | 8/2015 | Albers et al. | |
| 2017/0190617 A1 | 7/2017 | Hill et al. | |
| 2018/0134899 A1* | 5/2018 | Mulqueen | ................. C09C 1/48 |
| 2020/0140692 A1 | 5/2020 | Albers et al. | |

FOREIGN PATENT DOCUMENTS

| | | |
|---|---|---|
| WO | 9105734 | 5/1991 |
| WO | 9204414 | 3/1992 |

* cited by examiner

*Primary Examiner* — Stuart L Hendrickson
(74) *Attorney, Agent, or Firm* — Dentons Davis Brown; Matthew Coryell

(57) ABSTRACT

Disclosed is a method for producing a carbon black pigment from a microbial biomass. In certain aspects, the method involves providing a microbial biomass solution with a plurality microbial cells in an aqueous solvent; nucleating the plurality of microbial cells by adding a first soluble ion to the microbial biomass solution; initiating crystal formation in and/or on the plurality of microbial cells by adding a second soluble ion to the microbial biomass solution, forming a plurality of crystal encrusted microbial cells, where the charge of the first soluble ion is the opposite of the charge of the second soluble ion and where the crystals are formed from precipitation of the first and second ions; and performing thermal processing of the plurality of crystal encrusted microbial cells to form a charred biomass; washing the charred biomass to form a microbechar.

21 Claims, 6 Drawing Sheets

Table 1
| | Unsalted prior to charring | Salted prior to charring |
|---|---|---|
| Spirulina biomass | No/low flowability | High flowability |
| Yeast biomass | No/low flowability | High flowability |
FIG. 3C
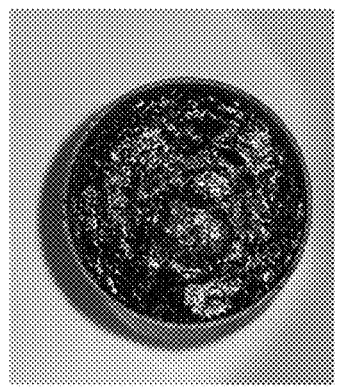
FIG. 4A
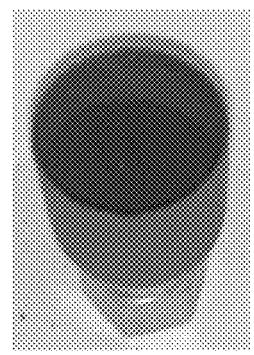
FIG. 4B
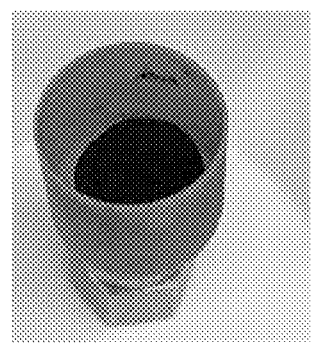
FIG. 5A
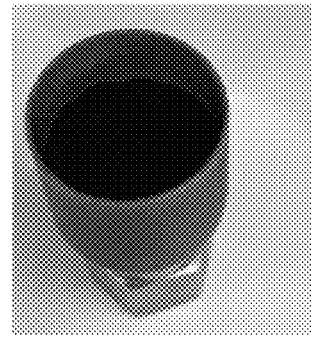
FIG. 5B Table 2

| Yeast (L value) | NO acid wash post charring | Acid wash post charring |
|---|---|---|
| unsalted prior to charring | 23.69 | 18.90 |
| Yeast biomass salted prior to charring | 24.34 | 15.96 |

Table 3

| Sample | AVG. L | AVG. A | AVG. B | Flowability |
|---|---|---|---|---|
| Yeast biomass unsalted prior to charring | 23.69 | 1.03 | 1.14 | Low |
| Yeast biomass unsalted prior to charring and acid washed post charring | 18.90 | 0.06 | 0.01 | Low |
| Yeast biomass salted prior to charring | 24.34 | 1.05 | 1.38 | High |
| Yeast biomass salted prior to charring and acid washed post charring | 15.96 | 0.43 | 1.30 | High |

Table 4

| Nannochloropsis | AVG. L | AVG. A | AVG. B | Flowability |
|---|---|---|---|---|
| Nannochloroposis biomass unsalted prior to charring | 24.34 | 0.05 | -0.16 | Low |
| Nannochloroposis biomass unsalted prior to charring and acid washed post charring | 19.10 | 0.31 | 0.45 | Low |
| Nannochloroposis biomass salted prior to charring | 21.86 | 0.65 | 0.13 | High |
| Nannochloroposis biomass salted prior to charring and acid washed post charring | 14.11 | 0.35 | 1.17 | High |

FIG. 6

BIOLOGICALLY-DERIVED CARBON BLACK ALTERNATIVE AND METHOD OF MAKING THE SAME

CROSS-REFERENCE TO RELATED APPLICATION(S)

This application claims priority to U.S. Provisional Application No. 63/021,494, filed May 7, 2020 and entitled "BIOLOGICALLY-DERIVED CARBON BLACK ALTERNATIVE AND METHOD OF MAKING THE SAME," which is hereby incorporated by reference in its entirety under 35 U.S.C. § 119(e).

TECHNICAL FIELD

The disclosed technology relates generally to the production of pigments and colorants from microbial biomass.

BACKGROUND

Pigments and colorants represent an over $30 billion a year industry. Yet the production of these compositions is associated with the production of toxic bioproducts that can harm human health and the environment. Prior attempts to generate pigment from non-toxic biomass have been limited in their ability to produce sufficiently small particle size to be suitable for most industrial applications. Thus, there is a need in the art for a method to produce pigments/colorants from sustainable sources that are suitable for industrial needs.

BRIEF SUMMARY

Disclosed is a method for producing a carbon black pigment from a microbial biomass. In certain aspects, the method involves providing a microbial biomass solution with a plurality microbial cells in an aqueous solvent; nucleating the plurality of microbial cells by adding a first soluble ion to the microbial biomass solution; initiating crystal formation in and/or on the plurality of microbial cells by adding a second soluble ion to the microbial biomass solution, forming a plurality of crystal encrusted microbial cells, where the charge of the first soluble ion is the opposite of the charge of the second soluble ion and where the crystals are formed from precipitation of the first and second ions; and performing thermal processing of the plurality of crystal encrusted microbial cells to form a charred biomass; washing the charred biomass to form a microbechar.

In certain embodiments, the first ion is an anion and the second ion is a cation. In further embodiments, the first ion is a cation and the second ion is an anion. In exemplary implementations of these embodiments, the cation is calcium and the anion phosphate. According to certain embodiments, the first ion and second ion are present at a stoichiometric ratio.

In certain aspects, the nucleating step may include performing a nucleation incubation by incubating the first ion with plurality of microbial cells for a period of from about 5 minutes to about two hours. The incubation step further may include heating the microbial biomass solution to a temperature from about 32° C. to about 65° C. The incubation step further may include agitating the microbial biomass solution. In certain embodiments, the agitating step is performed through sheer mixing the microbial biomass solution at about 2000 rpm for about two minutes.

In certain embodiments, the crystal formation step further may include crystallization incubation. In certain implementations, this step is performed by incubating the microbial biomass solution for a period of from about 5 minutes to about two hours. In certain implementations, the crystal formation step results in the formation of a plurality of crystal encrusted microbes with cell surface crystal formation and/or intracellular crystal formation.

In certain embodiments, the microbial biomass is comprised of a plurality of prokaryotic cells, where the average cell size of the prokaryotic cells is below about 50 µm.

In certain embodiments, the microbial biomass is dried at a temperature of from about 30° C. and about 300° C., prior to the thermal processing step and the microbial biomass is dried until moisture content is reduced to below about 15%. In certain implementations, the thermal processing steps is performed until the charred biomass has an amount of fixed carbon from about 20% to about 70%. In further implementations, the thermal processing step is performed until the concentration of oxygen is from about 10 and 15%.

In certain embodiments, the wash of the charred biomass is an acid wash. In exemplary implementations, the acid wash is performed by washing the charred biomass is a solution having a pH of below about 2. In certain implementations, this wash is performed for a time interval of from about 1 minute to about 1 hour. In exemplary embodiments, the acid wash and subsequent water wash produce a porous microbechar.

According to certain embodiments, a grinding step is performed on the microbechar following the acid wash step to form a milled microbechar. In certain implementations, the grinding step is performed until the average particle size diameter of the milled microbechar is less than about 10 µm.

In certain aspects, the carbon black pigment produced by the instantly disclosed process has increased flowability relative to microbial biomass with comparable thermal processing without being treated by the crystal formation step. Furthermore, the carbon black pigment produced has increased porosity relative to microbial biomass with comparable thermal processing without being treated by the crystal formation step. In further embodiments, the carbon black pigment produced has increased jetness relative to microbial biomass with comparable thermal processing without being treated by the crystal formation step.

In a further aspect, disclosed is a method for producing an engineered carbon black pigment from a microbial biomass. The method also includes performing thermal processing of the microbial biomass, where the microbial biomass may include a plurality of crystal encrusted microbial cells to form a charred biomass; and washing of the charred biomass is an acid wash, where the washing step may include reducing the pH of the charred biomass to below about 2 for a time interval from about 1 minute to about 1 hour to form a microbechar.

In a further aspect, disclosed is an engineered carbon black pigment may include: a charred biomass derived from a microbial biomass with a particle size of between about 0.01 microns and about 100 microns.

While multiple embodiments are disclosed, still other embodiments of the disclosure will become apparent to those skilled in the art from the following detailed description, which shows and describes illustrative embodiments of the disclosed apparatus, systems and methods. As will be realized, the disclosed apparatus, systems and methods are capable of modifications in various obvious aspects, all without departing from the spirit and scope of the disclosure.

Accordingly, the drawings and detailed description are to be regarded as illustrative in nature and not restrictive.

BRIEF DESCRIPTION OF THE DRAWINGS

FIG. 3C shows Table 1 with data on salting effects, according to certain embodiments.

FIG. 4A shows charred spirulina biomass that was washed of all salts prior to charring, according to one embodiment.

FIG. 4B shows charred spirulina biomass that was treated with a soluble anion/cation mixture prior to charring, according to one embodiment.

FIG. 5A shows pure untreated charred yeast biomass that was washed of all salts prior to charring, according to one embodiment.

FIG. 5B shows charred yeast biomass that was treated with a soluble anion/cation mixture prior to charring, according to one embodiment.

FIG. 6 shows Table 2-4 showing the effects of various treatments on flowability, according to certain embodiments.

DETAILED DESCRIPTION

Figure 1A:
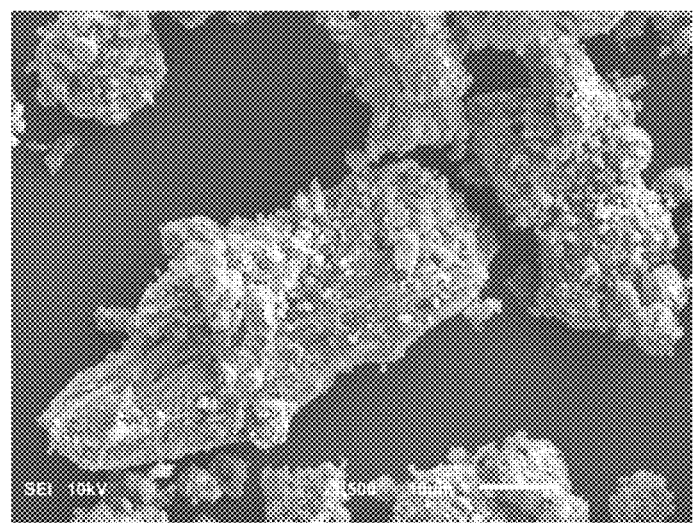
FIG. 1A is an scanning electron micrograph (SEM) image of charred Spriulina biomass (Arthrospira) that has been treated with a soluble anion/cation mixture prior to charring, according to one embodiment.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "microbechar" means the post thermal processing charred biomass produced according to the instantly disclosed methods. Microbechar can function as a carbon black pigment without further modification. Depending on the intended purpose, microbechar can also be further processed by mechanical (e.g. milling) or chemical (e.g. acid/base washes) means. Methods of modifying/processing microbechar are disclosed in U.S. patent application Ser. No. 16/677,644 (Publication No. US-2020-014069), which is incorporated herein by reference for all purposes.

Disclosed herein is a method for producing an engineered carbon black pigment from a microbial biomass by thermal processing of the microbial biomass, where the microbial biomass is comprised of a plurality of crystal encrusted microbial cells. The result of the thermal processing is the formation of a charred biomass. In certain implementations, the method further comprises grinding the charred biomass to a particle size of between about 0.01 microns and about 100 microns to form a milled microbechar.

In certain aspects, the disclosed method is a method producing a carbon black pigment from a microbial biomass comprising providing a microbial biomass solution comprising a plurality microbial cells in an aqueous solvent; nucleating the plurality of microbial cells by adding a first soluble ion to the microbial biomass solution; initiating crystal formation in and/or on the plurality of microbial cells by adding a second soluble ion to the microbial biomass solution, forming a plurality of crystal encrusted microbial cells, wherein the charge of the first soluble ion is the opposite of the charge of the second soluble ion; performing thermal processing of the plurality of crystal encrusted microbial cells to form a charred biomass, washing the charred biomass; and grinding the charred biomass to a particle size of between about 0.01 microns and about 100 microns to form a milled microbechar.

Microbial Biomass

Biological material is composed mainly of carbohydrates, protein and lipid. When these molecules are subjected to pyrolysis at 500-600° C., they undergo complex depolymerization and dehydration reactions, followed by a variety of fragmentation, elimination and condensation reactions to produce non-condensable volatiles, condensable vapor (liquid tar after cooling) and a carbonaceous char as the solid residue.

Carbohydrates are molecules consisting of carbon, hydrogen and oxygen. Within the cell, carbohydrates are normally stored as long-chained polysaccharides, such as cellulose and hemicellulose (woody plants), starch (plants and algae), and glycogen (cyanobacteria, fungi, bacteria). Glycogen is the main stored form of carbohydrate in cyanobacteria, such as Spirulina. It is a large, extensively branched polysaccharide of glucose, and has a structure similar to starch, but with a higher degree of branching. The pyrolysis of glycogen at high temperature (above 500° C.) generates similar products to those obtained from starch. These products include water, carbon monoxide, ethane, formaldehyde, ketene, propene, carbon dioxide, acetaldehyde, formic acid, acrolein, hydroxyacetaldehyde, pyruvaldehyde, hydroxypropane, 2-furaldehyde, furfurylalcohol, 5-mtehyl-2-furaldehyde, levoglucosenome, 5-hydroxymethyl-2-furaldehyde and levoglucosan. Many of these products are lost as volatiles, while others form the solid residual carbonaceous char.

Polysaccharides, such as glycogen, may be broken down into their smaller monosaccharide building blocks through a hydrolysis reaction. One method of glycogen hydrolysis involves the application of heat and a dilute acid to hydrolyze glucose units from the glycogen branches. This reaction readily occurs at 100° C. When monosaccharide units, such as glucose heated to 160° C. they undergo a process call caramelization, when crystalline sugar melts into clear molten sugar. As the temperature increases to 165° C. the molten sugar can be poured, but will become hard, glasslike and brittle when cooled. Further heating to 210° C. causes a softer, stickier texture when cooled. When glucose is pyrolyzed to 500° C., the main products can be classified into three primary categories: (1) low molecular weight compounds, (2) furan/pyran ring derivatives and (3) anhydro sugars. Biological material that has a high monosaccharide/simple sugar content, may show melting characteristics during the pyrolysis heating process to 500° C., and a mushrooming effect of the biomass due to the release of volatiles within the sticky mass.

Proteins are polymer chains of amino acids linked by peptide bonds, and are highly susceptible to heat denaturation at temperatures as low as 40° C. The process of denaturation involves breaking the weak bonds within the protein molecule to cause structural changes. Subsequent coagulation of denatured proteins will often occur where the protein will "set" as a solid or thick liquid, and is a process that is irreversible when cooled. Exposure to the extreme temperatures of pyrolysis will cause proteins to thermally decompose via pathways of decarboxylation, deamination, hydrocarbon residue fragmentation, dimerization and fragmentation of peptide bonds to form amide/amines/nitriles, esters, hydrocarbons and N-heterocyclic compounds, especially diketopiperazines (DKPs).

Lipids are also susceptible to heat decomposition. When heated in the presence of moisture, the ester linkages of lipids hydrolyzed to release free fatty acids. During pyrolysis, lipids thermally decompose via pathways that include: dehydration, decarboxylation, hydrolysis of ester bond, double bond conjugation, polymerization, dehydrocyclization, aromatization, dehydrogenation, and degradation by carbon-carbon cleavage.

According to certain embodiments, the microbial biomass for the disclosed process may be derived from a number of microbial sources. In certain implementations, the microbial biomass is comprised of a plurality of microbial cells. In certain embodiments, these cells (or groups of cells) have an average size from about 10 nanometers and about 300 micrometers. the starting material may have one or more of the following characteristics: cells originating from single celled, colonial, multi-cellular or filamentous organisms, intact cells, cells or cell masses that exhibit a sphere-like shape, cells in which certain cellular components are removed prior to thermal treatment, and/or cells in a solution or may be cells that have been removed from a solution.

The plurality of cells comprising the microbial biomass can acquire energy by chemotrophy, heterotrophy, or autotrophy. In certain the embodiments, the microbes are eukaryotic. In alternative embodiments, the microbes are prokaryotic. In certain further embodiments, the plurality of microbial cells comprising the microbial biomass is a mixture of any of the foregoing microbes, such as that which is found in a body of water in nature.

Various implementations utilize colony forming types of bacteria, algae and cyanobacteria. In various implementations, plurality of cells of the microbial biomass aggregate diameters of smaller than 300 microns. One aspect of the disclosure relates to implementations where the pigment portion is about 0.01-300 microns. It is understood that this size allows an increase in the amount of pigment particles to disperse to an acceptable density so that dark colors can be attained. In various implementations, the 0.01-300 microns size can be achieved in several ways. In certain implementations, the size can be achieved by growing an appropriately sized biological cell. In alternate implementations, the size can be achieved by grinding the cells or cell aggregates to the correct size (0.01-300 microns). In yet another implementation, both cells with 0.01-300 microns in diameter as well as grinding of cells or aggregates may be used.

According to certain implementations, the microbial biomass is comprised of plurality of microbial cells. Microbial cells suitable for the disclosed method of microbes include heterotrophic, autotrophic, mixotrophic, or extremophillic microorganisms, including microalgae, algae, macro algae, cyanobacteria, fungi, and bacteria. In certain implementations, the plurality of cells are a mixture of the forgoing. According to certain embodiments, the microbes comprising the plurality of microbial cells is one or more selected from the following: *Synechocystis* PCC 6803, *Synechococcus* PCC 6717, *Synechococcus* PCC 6301, *Synechococcus* IU 625, *Synechococcus* PCC 6312 *Synechococcus elongatus* PCC 7942, *Nostoc* sp., *Synechococcus* 6911, *Synechococcus leopoliensis, plankthorax rubescens, Synechococcus* PCC 7002, *Arthospira platensis* PCC 7345, *Haematococcus pluvailis, Navicula pelliculosa, Cryptomonas erosa, Rhodomonas minuta, Porphyridium purpureum, Phaeodactylum tricornutum, Nannochloropsis* sp. *Synechocystis* sp., *Synechococcus* sp., *Nostoc* sp., *plankthorax* sp., *Arthospira* sp., *Haematococcus* sp., *Navicula* sp., *Cryptomonas* sp. *Rhodomonas* sp. *Porphyridium* sp., *Phaeodactylum* sp., *Nannochloropsis* sp., *Volvox* sp., *Anabena* sp., *Chlorella* sp., *Euglena* sp., *Achnantes* sp., *Botryococcus* sp., *Chaetoceros* sp., *Chroococcus* sp., *Cosmarium* sp., *Microcystis* sp., *Microspora* sp., *Pediastrum* sp., *Scenedesmus* sp., *Spirogyra* sp., *Spirulina* sp., *Zygnema* sp., *Chlorobium* sp., *Escherichia* sp., *Spirillum* sp., *Chromobacterium* sp., *Janthinobacterium* sp., *Streptomyces* sp., *Xanthomonas* sp., *Sarcina* sp., *Serratia* sp., *Rhizobium* sp., *Prevotela* sp., *Actinomyces* sp., *Staphylococcus* sp., *Proteus* sp., *Micrococus* sp., *Rugamonas* sp., *Pseudomonas* sp., *Helicobacter* sp., *Saccharomyces* sp., *Candida* sp., *Leucosporidium* sp., *Rhodotorula* sp., *Schizosaccharomyces* sp., *Dekker* sp., *Brettanomyces* sp., *Synechocystis* sp., *Synechococcus* sp., *Nostoc* sp., *planktho-* rax sp., *Arthospira* sp., *Haematococcus* sp., *Navicula* sp., *Cryptomonas* sp. *Rhodomonas* sp. *Porphyridium* sp., *Phaeodactylum* sp., *Nannochloropsis* sp., *Volvox* sp., *Anabena* sp., *Chlorella* sp., *Euglena* sp., *Achnantes* sp., *Botryococcus* sp., *Chaetoceros* sp., *Chroococcus* sp., *Cosmarium* sp., *Microcystis* sp., *Microspora* sp., *Pediastrum* sp., *Scenedesmus* sp., *Spirogyra* sp., *Spirulina* sp., *Zygnema* sp., *Chlorobium* sp., *Escherichia* sp., *Spirillum* sp., *Chromobacterium* sp., *Janthinobacterium* sp., *Streptomyces* sp., *Xanthomonas* sp., *Sarcina* sp., *Serratia* sp., *Rhizobium* sp., *Prevotela* sp., *Actinomyces* sp., *Staphylococcus* sp., *Proteus* sp., *Micrococus* sp., *Rugamonas* sp., *Pseudomonas* sp., *Helicobacter* sp., *Saccharomyces* sp., *Candida* sp., *Leucosporidium* sp., *Rhodotorula* sp., *Schizosaccharomyces* sp., *Dekker* sp., and *Brettanomyces* sp. One skilled in the art will appreciate that other microbes are possible.

According to certain embodiments, the diameter of each of the intact microbial cells is less than about 300 microns. According certain implementations of these embodiments, the microbe is *Haematococcus* , *Euglena*, and/or *Odontella* sp.

According to further implementations, the diameter of each of the intact microbial cells is less than about 10 microns. According certain implementations of these embodiments, the microbes may be one or more of the following: *Plankthorax* sp., *Arthospira* sp., *Synechocystis* sp., *Synechococcus* sp., *Nostoc* sp., *Plankthorax* sp., *Arthospira* sp., *Haematococcus* sp., *Navicula* sp., *Cryptomonas* sp. *Rhodomonas* sp. *Porphyridium* sp., *Phaeodactylum* sp., *Nannochloropsis* sp., *Achnantes* sp., *Botryococcus* sp., *Chaetoceros* sp., *Chroococcus* sp., *Cosmarium* sp., *Microcystis* sp., *Microspora* sp., *Pediastrum* sp., *Scenedesmus* sp., *Spirogyra* sp., *Spirulina* sp., *Zygnema* sp., *Chlorobium* sp., *Escherichia* sp., *Spirillum* sp., *Chromobacterium* sp., *Janthinobacterium* sp., *Streptomyces* sp., *Xanthomonas* sp., *Sarcina* sp., *Serratia* sp., *Rhizobium* sp., *Prevotela* sp., *Actinomyces* sp., *Staphylococcus* sp., *Proteus* sp., *Micrococus* sp., *Rugamonas* sp., *Pseudomonas* sp., *Helicobacter* sp., *Saccharomyces* sp., *Candida* sp., *Leucosporidium* sp., *Rhodotorula* sp., *Schizosaccharomyces* sp., *Dekker* sp., *Brettanomyces* sp., *Lactobacillus* sp., *Pyrococcus* sp., *Corynebacterium* sp., *Aspergillus* sp., *Bacillus* sp., *Streptococcus* sp., *Acetobacter* sp., *Clostridium* sp., *Trichoderma* sp., *Penicillium* sp., *Prochlorococcus* sp., *Anabena* sp., *Chlorella* sp., *Thermosynechococcus* sp., *Chlamydomonas* sp., *Gloeocapsa* sp., *Anabaenopsis* sp., *Calothrix* sp., *Oscillatoria* sp., *Gloebacter* sp. *Cyanidioschyzon* sp., *Crypthecodinium* sp., and/or *Galdieria* sp.

In certain embodiments, the plurality of microbial cells comprising the microbial biomass are comprised of intact whole cell microbes. In alternative embodiments, the microbial biomass is comprised of disrupted microbial cells (e.g. the integrity of the cell wall and/or cellular membrane has been disrupted). In certain aspects of these embodiments, the microbial biomass is comprised of disrupted microbial cell components. According to certain implementations of these embodiments, one or more microbial components is depleted from the microbial biomass. In exemplary implementations, lipids, amino acids, carbohydrates, minerals, and/or colorant molecules are depleted from the microbial biomass.

In certain implementations, the cells may have cellular components extracted from the overall biomass. In exemplary embodiments, these cellular components are one or more of carbohydrates, proteins, fats, minerals, nucleic acid material and/or any combination of the foregoing.

In certain implementations, the plurality of microbial cells making up the microbial biomass are treated to remove certain cellular components, prior to thermal treatment. Exemplary treatments included, but are not limited to: salting in/out, cold maceration, ultrasonication, high pressure homogenization, freeze thaw, acid extraction, base extraction, organic extraction, inorganic extraction, lysozyme extraction, mechanical extraction, membrane filtration, and/or high pressure extraction.

In certain embodiments, the microbial biomass is prepared for processing in a microbial biomass solution. In exemplary implementations, the microbial biomass is dissolved into an aqueous solvent to make the microbial biomass solution. In certain embodiments, the aqueous solvent is water.

Nucleation and Crystal Formation

In certain aspects, the disclosed method involves the step of causing the formation of crystals on the cell surface and/or within intracellular space of the plurality of microbial cells comprising the microbial biomass. In certain embodiments, the step of causing cellular crystal formation is comprised of two steps: a nucleation step and crystal formation step. In exemplary implementations, the nucleation steps is performed by adding a first soluble ion to the microbial biomass solution and the crystallization step is performed by adding a second soluble ion to the microbial biomass solution wherein the charge of the first soluble ion is the opposite of the charge of the second soluble ion (e.g., if the charge of the first ion is positive, the charge of the second ion is positive, and if the charge of the first ion in negative, then the charge of the second ion is positive). The first and second ions bind to form insoluble crystal on the cell surface and/or within the cellular void.

In certain embodiments, the first ion is an anion and the second ion is a cation. In certain alternative embodiments, the first ion is a cation and the second ion is an anion. In exemplary embodiments, the first and second ion are sequentially added to the microbial biomass solution through the addition of a first and second ionic solution, respectively. Such a first and second ionic solutions can be prepared by dissolving a soluble salt of the ion in an aqueous solvent (e.g. water). In exemplary implementations, upon the addition of the second ionic solution to the microbial biomass, the first and second ions precipitate and crystalize in/on the cells, while the counterions of the first and second ions remain highly soluble and in solution. In certain exemplary implementations of these embodiments, the cation is calcium and the anion phosphate. A calcium solution and phosphate solution are prepared (according to certain embodiments) through dissolving calcium chloride and sodium phosphate, respectively, in water. Upon addition of the second ion solution, calcium and phosphate form crystals in/on the cells while the sodium and chloride remained dissolved in solution.

In further embodiments, the first and second ion can be any ion pair that precipitate/crystallize in the microbial biomass solution solvent. Exemplary ion pairs are shown in table 1, although these should not viewed as limiting. It should be understood that ions in columns A and B can each be either the first ion or second ion, according to certain embodiments.

TABLE 3

Exemplary precipitate for intracellular and surface crystallization.

| Precipitate | A | B | Solubility of precipitate (H2O) | Solubility of precipitate (other) | Melting point | pKa of precipitate |
|---|---|---|---|---|---|---|
| $CaHPO_4 \cdot 2H_2O$ brushite | CaCl | $Na_3PO_4$ | 0.2 g/100 mL (anhydrous) 0.2 g/100 mL (dihydrate) | NA | — decomposes to $CaHPO_4$ At ~100-220 C.- further Decomposes around 270-450 C. to $Ca_2O_7P_2$ | 12.2 |
| $Ca_2O_7P_2$ Calcium pyrophosphate | CaCl | $Na_4P_2O_7$ | Insoluble | HCl and nitric acid | 1,353° C. | NA |
| $Ca(OH)_2$ Calcium hydroxide | CaCl | NaOH | 1.73 g/L (20° C.) | Soluble in glycerol and acids. | 512-580° C. (loses water, decomposes into calcium oxide and water | 12.63 (first) 11.57 (second) |
| $CaSO_4$ Calcium sulfate | CaCl | $Na_2SO_4$ | 0.21 g/100 ml at 20° C. (anhydrous) 0.24 g/100 ml at 20° C. (dihydrate) | slightly soluble in glycerol | 1,460° C. (2,660° F.; 1,730K) (anhydrous) | 10.4 (anhydrous) 7.3 (dihydrate) |
| $CaCO_3$ Calcium carbonate | CaCl | $Na_2CO_3$ | 0.13 g/L (25° C.) | Soluble in dilute acid | 825° C. | 9.0 |

In certain embodiments, first ion and second ion are present at a stoichiometric ratio. In further embodiments, the first and second ion are present at a ratio of from about 2:1 to about 1:2.

While in some embodiments, a given combination of anion and cation can be added sequentially in either order, in certain embodiments, one must be added before the other. For example, for calcium chloride and sodium phosphate, order is important in certain embodiments. Independently, these ions are highly soluble in aqueous solutions. The addition of two mixtures containing these ions produces insoluble calcium phosphate and highly soluble sodium chloride. The choice of the calcium ion and phosphate ion is notable because the microbial cell surface allows passive diffusion of extracellular calcium ions while phosphate ions are extremely prevalent in most living cells. Swelling of microbial biomass in calcium chloride solution is beneficial as the surface of microbial cells tends toward negative charges which will attract positive calcium ions into the cell membrane and further into the internal space of the cells. This allows a high concentration of calcium ions in the cells that leads to a high degree of crystallization when the sodium phosphate solution is added. However, when swelling of algae in sodium phosphate solution is attempted, the phosphate will be rejected from the membrane and stay in the solution outside of cells. Upon the addition of calcium chloride, the precipitates will mostly form outside of the cells.

Turning back to the nucleation step, also referred to herein as the nucleating step, the addition of the first ion into the microbial biomass solution allows the first ion to bind to sites on the cell surface and within the cell, providing for a nucleation site for future crystal growth. In certain embodiments, the nucleating step further comprises performing a nucleation incubation by incubating the first ion with plurality of microbial cells for a period of from about 1 minute to about 24 hours. In further implementations, incubation is for a period of from about 5 minutes to about two hours In yet further implementations, the incubation step is about 1 hour.

In certain embodiments, the incubation step further comprises heating the microbial biomass solution to a temperature from about 32° C. to about 65° C.

In still further embodiments, the nucleation step further comprises performance of an agitation step, aimed increasing penetration of the first ion into the cell. In certain implementations, agitating step is performed through sheer mixing the microbial biomass solution at about 2000 RPM for about two minutes. In alterative implementations, the agitation step is performed through sonication.

Turning now to the crystal formation step, following the nucleating step, the second ion is added to the microbial biomass solution and precipitation/crystal formation proceeds at the nucleation sites on/in the cells. The formation of such crystals gives rise to a plurality of crystal encrusted microbes. In certain embodiments, the crystal formation step further comprises performing a crystallization incubation by incubating the microbial biomass solution for a period of from about 1 minute to about 24 hours. In further implementations, the crystallization incubation is for a period of from about 5 minutes to about two hours In yet further implementations, the incubation step is about 1 hour. In certain implementations, the crystallization incubation is at about 25° C.

In certain embodiments, the plurality of crystal encrusted microbes has cell surface crystal formation. In further embodiments, the plurality of crystal encrusted microbes has intracellular crystal formation. IN further embodiments, the plurality of crystal encrusted microbes has both cell surface and intracellular crystal formation.

According to certain alternative embodiments, supersaturation and slow cooling is another way to grow crystals in a controlled manner (cooling of solution). Solubility of most compounds increases with increasing temperature. For example, trisodium phosphate (Na3PO4) : 5.4 g/100 mL (0° C.); 12 g/100 mL (20° C.); 14.5 g/100 mL (25° C.); 23.3 g/100 mL (40° C.); 94.6 g/100 mL (100° C.). 94.6 g of trisodium phosphate can be dissolved in 100 ml of water 100° C. When this solution is cooled to 0° C., 89.2 g of sodium phosphate will precipitate. Calcium chloride also has a similar solubility trend where the increase temperature leads to the increased solubility: 49.4 g/100 mL (−25° C.), 59.5 g/100 mL (0° C.), 65 g/100 mL (10° C.), 81.1 g/100 mL (25° C.), 102.2 g/100 mL (30.2° C.). There are a limited set of compounds that exhibit reverse solubility trends. For example, Calcium hydroxide (Ca(OH)2) has a decreasing solubility trend with the increasing temperature: 1.89 g/L (0° C.), 1.73 g/L (20° C.), 0.66 g/L (100° C.), in which case the increasing temperature will lead to precipitation. The supersaturation method can result in both intracellular and extracellular crystals, depending on the chemical species, algae species, and concentrations, etc. microbial cells perform as nucleating agents. An advantage of this method is recyclability of mineral added for the sequential treatments and ease of char washing due to highly soluble mineral added. An example treatment is conducted as following: 100 g of calcium chloride is dissolved in 100 mL of DI water at 30° C. 8 wt % of algae is then added to the calcium chloride solution, which is sheared with a shear mixer for 5 mins at 2000 RPM and then stirred at 30° C. for 1 hr. The solution is then cooled to 25° C., which was maintained for 10 mins. This solution with precipitate was centrifuged and dried.

According to further alternative embodiments, another crystal formation method is controlled drying (Solvent evaporation). In exemplary implementations, as the solvent is evaporating, the total capacity of soluble compounds decreases as the amount of solvent is decreasing although the solubility of the solvent stays the same due to the constant environment. With sufficient evaporation, the solvated compounds will precipitate out as growing crystals. For example, 81 g of calcium chloride can be dissolved in 100 mL of water at 25° C. If 100 mL of water is evaporated to 50 mL 25 C, 40 g of calcium chloride will be precipitated out. Microbial cells will perform as nucleating agents. The advantage of this method is scalability and recyclability.

In yet further alternative embodiments, a further crystallization method is mixing of poor solvent into ionic solution (solvent mixing). Each compound has solvents that can dissolve the said compound and cannot dissolve. The former is called good solvent, the latter poor solvent. Trisodium phosphate has a very high solubility in water (aka good solvent) while is not soluble in ethanol (aka poor solvent). Therefore when ethanol is added to the aqueous solution of trisodium phosphate, the solubility of solution (ethanol+water) gradually decreases as the mixed solution changes from good solvent to poor solvent. This change results in crystallization. The example treatment is following: 14 g of trisodium phosphate is dissolved in 100 mL of DI water at 25 C. 8 wt % of algae is then added to the calcium chloride solution, which is sheared with a shear mixer for 5 mins at 2000 RPM and then stirred at 25 C for 1 hr. 50 mL of ethanol is then added. The mixture is filtered and dried.

As will be appreciated, each crystallization method can be compatible with other crystallization methods. For example, the hot supersaturated solution can be cooled and added with a poor solvent to produce crystals. The methods listed here are not comprehensive. Other crystal growth methods includes deposition from gas (e.g. chemical vapor deposition).

Without wishing to be bound by theory, it is believed that the crystal formation treatment creates 1) dendritic crystal growth on the cell surface to act as a physical barrier and keep the cells separate during charring that prevents cells from fusing together by melting from the temperature. The melting temperature of most carbohydrate, lipids, and proteins are below 200 C while the temperatures applied during thermal processing may be in excess of 500 C. 2) the crystal growth within the cellular void to shear the cell membranes while keep internal folds from bonding to each other, producing high porosity that contributes to high black coloration. 3) mineral-based heat distributor that evenly chars the biomass from the surface and the internal space. Thermal conductivity of common biomass is ~0.1 W/m/K while that of common mineral is an order of magnitude higher (~1 W/m/K).

In certain alternative embodiments, dry powder of salts can be directly added to the biomass. These added crystals can be either ion precursors or precipitates, or any other minerals. Preferably these mineral powders have anti-caking properties while having a melting temperature higher than the charring temperature. These mineral additives include but are not limited to tricalcium phosphate, dicalcium phosphate, magnesium silicate, silicon dioxide, and/or sodium aluminosilicate. The size of mineral additives are preferably equal to or an order of magnitude smaller than the biomass particles, more preferably two orders of magnitude smaller. The size of many microorganism biomasses range from 1 micrometer to tens of micrometers and larger. Therefore the size of these additives is preferably in single digit micrometers. These mineral powders can be applied by various coating methods including but not limited to a fluidized bed, powder coat spray, co-grinding using various mills, etc. Dry mineral precipitates are added to the microbial biomass, which may be in either solution or in a dry form. These embodiments may include the step of adding minerals and/or other conversion and binding agents to the biomass. These minerals act in a way to stabilize the biomass and/or components found in the biomass such that no substantial change in the size and structure of the biomass occur during the thermal processing.

In exemplary implementations of these embodiments, added minerals make up from about 0.1 to about 70% of the overall mass of the sample. In certain implementations, minerals may be added in any state of matter (e.g., gas, liquid, or solid). In certain embodiments, minerals cause simple carbohydrates to volatilize more quickly, thus causing the biomass to NOT stick together while charring Without wishing to be bound to any particular theory, it is contemplated that minerals may perform one or more of the flowing functions: i) cause a change in the electromagnetic surface "charge" of the particles through a change of the functional groups found on the surface of the particles themselves; ii) act as distinct heating units that "burn" through the cell wall/membrane in distinct areas- Minerals absorb thermal energy and dissipate this energy in very distinct areas at very high temperature. This causes specific locations on the biomass surface to experience "hot spots" on the surface, where localized regions experience increased temperatures and thus, unique reactions that create new organic species within small regions surrounding the mineral biomass. As the minerals are washed away in a washing step occurring after the charring process, distinct holes within the organic matter to appear and cause the appearance of "fuzzy spheres" on the char particles iii) act as a "binder", capable of modification of the evolution of various products within the biomass as it is charred; iv) participate in reactions that lowers the overall amount of gaseous oxygen species produced. This occurs as the various minerals added to the biomass perform reactions capable of removing oxygens from organic matter found in the biomass; v) cause the degradation of carbohydrates into alternative forms of organic matter, thus reducing the amount of structural conversion that leads to the "melting" of the biomass; vi)accelerate the degradation of organic matter into gaseous species, thus decreasing the amount of biomass that "liquefies" within the sample; and/or vii) contribute elements that cause structural changes to the biomass constituents.

Biomass contains organic matter—protein, carbohydrates and lipids as well as inorganic elements which can be both endogenous and exogenous minerals. The minerals are alkali, alkaline and transition metals for example, Ca, K, Si, Mg, Al, S, Fe, P, Cl, Na and some trace metals. These minerals can vary among difference species. Woody biomass contains less ash from Cl, K, N, S and Si but contains more Ca and Mg. Minerals are known to stabilize biochar by oxidation resistance during pyrolysis. Especially, alkali and alkaline earth metals catalyzes biomass decomposition and char-forming reactions. Pretreatment to reduce ash content often results in lower charcoal yield. Impregnation with Fe can impact the degree of aromatic condensation and the porosity of biochar. Similarly, certain alkali metals like K and Na can react with chlorine to form gaseous compounds such as KOH, KCl, $K_2SO_4$, NaCl, $Na_2SO_4$ released in the gas phase. Si, k and Ca are main elements responsible for agglomeration to form CaO, $SiO_2$, $K_2O$ due to their fusibility tendencies. Minerals can catalyze secondary reactions by reacting with certain sugar byproducts such as levoglucosan to form other volatiles such as levoglucosenone, furan derivatives and lighter oxygenates. The presence of high mineral content in biomass affects product distribution by lowering oil yield and increased char and gas products. The catalytic activity of ash changes the dynamics of combustion and gasification. Reducing the ash content of biomass by washing has been shown to increase the temperature of peak combustion but decrease the temperature of peak gasification mass loss rate.

In further implementations, additions to the biomass include the addition of species that convert simple carbohydrates into gaseous species. Further implementations include the addition of binders capable of sequestering simple carbohydrates and/or proteins.

Drying Microbial Biomass

In certain aspects, the microbial biomass is dried to reduce moisture content and concentrate the cells. In certain implementations, the microbial biomass is dried until moisture content of from about 10%- to about 20% is reached, for example 15%. In further embodiments, the microbial biomass is dried until the moisture content reaches about 5% or lower.

The drying step may be performed according to a variety of techniques know in the art. In exemplary embodiments, cells are dried by way of drum filtration, filtration/drying, dead-end filtration, microfiltration, ultra-filtration, pressure filtration, vacuum filtration, tangential flow filtration, diatomaceous earth filtration, membrane filtration, magnetic separation, forward osmosis, electrofloation, roller press, belt harvesters, capillary extraction, simple heating/evaporation, hydrocyclone, crossflow, assisted separation (magnetic, electric, dielectric, acoustic), granular bed filters, precoat filters, disc stack centrifugation, cross flow filtration, decanter centrifugation, spray drying, or organic flocculation. Drying may be accomplished by techniques described in Advancement and Challenges in Harvesting Techniques for Recovery of Microalgae Biomass, Difusa et. al, which is incorporated by reference herein in its entirety.

According to certain embodiments, the method further includes the step of drying the biomass. This drying step may be performed by way of in one a number of techniques known in the art. Exemplary drying methods include, but are not limited to: drum drying, spray drying, tray drying, pulse combustion drying, evaporative drying, convective drying, freeze drying, spiral plate drying, surface tension driers, vacuum tray driers, solar conduction driers, osmotic driers, membrane separation driers, sedimentation driers, flocculation driers, froth floatation separation, centrifugation separation, and or filtration.

In certain implementations, the drying steps removes from about 30 to about 99% of all solution from the biomass. In certain alternative implementations, the drying step is omitted from the disclosed method.

Thermal Processing

According to certain embodiments, following drying of the microbial biomass, the microbial biomass undergoes thermal processing to produce a microbechar. In certain aspects, thermal processing is performed in a reaction vessel. In exemplary implementations, the reaction vessel is capable of producing an air-tight seal, so to exclude any additional gasses from being introduced into the production process. In one embodiment, inert gasses can be added to the container so to force off any unwanted gasses like carbon dioxide, oxygen and any other reactive gas species. In certain alternative embodiments, air and other reactive gasses are added to the combustion chamber so to increase the overall combustion temperature and to facilitate chemical reactions within the chamber. In another embodiment, a various types of inert and reactive gasses may be introduced into the reaction chamber in successive steps to obtain various types of reactions at different points during the heating process. The suitable reaction vessels are comprised of a variety of reaction vessels known in the art. Exemplary reaction vessels, include, but are not limited to: batch reactors, rotary kilns (vertical or horizontal), shaft furnaces, fluidized bed, sprouted bed, entrained bed, screw reactors, herreshoff over/multiple hearth furnace, torbed reactor, microwave reactor, compact moving bed, belt drier/reactor, and fixed bed reactors.

In certain aspects, thermal processing of the cells is performed by way of a process selected from the group consisting of: pyrolysis, gasification, combustion, thermal-oxidative decomposition, torrefaction, and hydrothermal carbonization. In certain embodiments, the thermal processing step involves the use of a combination of the foregoing.

According certain implementations, the thermal processing step is at a temperature range from about 100° C. to about 2000° C. In certain further implementations, the temperature range is from about 100° C. to about 1000° C. In further aspects, the thermal processing temperature range is from 200° C. to about 800° C. . In further aspects, the thermal processing temperature range is from 250° C. to about 750° C. In further aspects, the thermal processing temperature range is from 300° C. to about 700° C. In further aspects, the thermal processing temperature range is from 350 ° C. to about 750° C. In still further aspects, In further aspects, the thermal processing temperature range is from 400° C. to about 700° C. In yet further implements, the thermal processing step is about 550° C. In certain exemplary implementations, the temperature is increased at stepwise intervals. In certain alternative implementations, the temperature is increased at a constant rate over a predetermined interval.

In certain aspects, the thermal processing step is performed at a time interval from about 1 second to about 24 hours. In further aspects, the time interval is from about the thermal processing step is performed at about 600° C. and for a time interval of about 5-7 minutes. According to certain implementations, the thermal processing step is performed until a predetermined endpoint is reached. According to exemplary implementations, the end point reached when the charred biomass is comprised of fixed carbon of from about 20% to about 75%. According to further embodiments, the end point reached when the charred biomass is comprised of fixed carbon of from about 20% to about 50%. In yet further embodiments, the end point reached when the charred biomass is comprised of fixed carbon of from about 20% to about 30%

In further embodiments, the thermal processing step is performed until the charred biomass is from about 15% to about 60% of initial starting mass In further embodiments, the thermal processing step is performed until the level of proximate volatiles in the charred biomass is below about 25%. In further embodiments, the thermal processing step is performed until the level of proximate volatiles in the charred biomass is below about 20%. In yet further embodiments, the thermal processing step is performed until the level of proximate volatiles in the charred biomass is between about 15% and about 25%.

In yet further embodiments, the thermal processing step is performed until the concentration of oxygen in the charred biomass is below about 20%. In still further embodiments, the thermal processing step is performed until the concentration of oxygen is from about 10 and 15%.

According to still further embodiments, the thermal processing step is performed until the concentration of ash in the charred biomass is below about 20%. According to certain further embodiments, the thermal processing step is performed until the concentration of ash in the charred biomass is between about 10% and 20%. In still further embodiments, the thermal processing step is performed until the concentration of ash in the charred biomass is below about 10%.

In certain aspects the thermo processing step endpoint is defined by a predetermined ratio of oxygen and fixed carbon. In exemplary implementations of these embodiments, the thermo processing endpoint is reached when the ultimate oxygen to ultimate carbon ratio of the charred biomass is below about 0.30 oxygen to carbon (e.g., 3 parts ultimate oxygen to 10 parts ultimate carbon).

In certain embodiments, the endpoint is reached when two or more of the foregoing parameters are reached.

Post Thermal Processing Washing

In further implementations, the disclosed method also includes the step of post-thermal processing washing/activation of the biomass. In exemplary implementations the wash may be performed by washing the charred biomass with materials that make the wash acidic or basic in nature. In exemplary embodiments, one or more of the following are used: muriatic acid, hydrochloric acid, bleach, phosphoric acid, potassium hydroxide, sodium hydroxide, calcium chloride, and zinc chloride. In certain implementations the concentration of acid or base is from about 0.2% to about 20% of the wash. IN certain implementations, where an acid wash is used, the wash has a pH of about −1.0 to about 6. In exemplary implementations, the wash has a pH of about 0.1 to about 3.0.

According to certain embodiments, the post-thermal processing wash is repeated from 1 to 10 or more times. In certain implementations, each wash may have a duration from about 30 seconds to about 12 hours. Such washing can serve to remove from about 60% to about 100% of the minerals present in/around/on the charred biomass.

In certain implementations, water washes are also included in the post thermal processing washing step. In certain embodiments, the water wash occurs before, after, or both before and after the acid/base wash(es).

Without wishing to be bound to any particular theory, it is believed that the post-char was step(s) serves one or more of the following functions: i) cause larger particles to be formed into smaller particles (e.g., dissolving biomass material that may cause cell adhesion and cell binding changes the surface area of the particles and the electromagnetic charges associated with the particles themselves); ii) the removal of mineral species that resulting in mineral content (ash content) to be between 1%-30% minerals of the overall mass of the material, in exemplary embodiments, ash content is below about 10%. This allows for a higher concentration of carbon to be present in the samples, thus more black material as mineral species are usually gray-white in color; iii) removes surface minerals that, when removed, allow for higher surface area while leaving volume of particles un-disturbed; iv) breakdown of cellular components that causes biomass to "stick" together more; acid washing may change the charge of the biomass.

Grinding

In certain embodiments, no grinding is required following the thermal processing step and the microbechar can be used as a pigment without further processing or with only chemical processing. However, in certain alternative embodiments, grinding of microbechar is required to attain a targeted pigment particle size or cell aggregate diameter of between the values 0.01 microns and 100 microns in particle diameter size. In certain embodiments, the grinding step is performed by way of an apparatus selected from the group consisting of: mortar/pestle, rotary tumbler, vibratory tumbler, magnetic tumbler, roll mills, bead mill agitator, disc mill, basket mill, jet mill, ball mill, jaw crusher, rotor mill, cutting mill knife mill, cryo mill, hammer mill, pin mill, cyclone mill, and classifier mill.

According to further embodiments, the grinding step is performed by way of a method selected from the group consisting of: ammonia freeze explosion, steam hydrolysis, and wet-oxidation.

According to still further embodiments, the grinding step is performed by way of ultrasonication.

According to certain embodiments, the grinding step is performed until the average particle size diameter of the milled microbechar is less than about 10 microns.

In certain implementations, the grinding step comprises adding one or more mechanical grinding additives to the charred biomass during grinding. According to further embodiments, the one or more mechanical grinding additives is selected from a list consisting of: steel, chrome, stainless steel, ceramic, rubber, stoneware, aluminum, magnesium, zirconia, porcelain, silica, and glass. According to certain further embodiments, the mechanical grinding additive has a particle size ranging from about 1/32 inch to about 5 inches in diameter.

In certain aspects, the grinding step comprises adding one or more chemical grinding additives to the charred biomass during grinding. In certain implementations of these embodiments, the one or more chemical grinding additive is selected from the list consisting of: dispersants, surfactants, wetting agents, burnishing compounds, soap detergents, hyperdispersants, nonionic high-HLB polyalkoxylated surfactants, non-ionic polymers, defoamers, water, resins, surface tension modifiers, hydrophobic anionic polymers, acetylenic diol, and acetylenediol.

Post-Grinding Modification of Milled Microbechar

According to certain embodiments, the disclosed method further comprises modifying the milled microbechar after the grinding step. In certain aspects, these post grinding modification steps seeks to reduce the individual particle size. In further aspects, these steps are carried to achieve desired properties of particle surface to make the microbechar suitable for specific applications. According to certain embodiments, post-grinding modification seeks to reduce the heavy metal content of the microbechar In further embodiments, post-grinding processing seeks to removes of soluble inorganic salts and or reduce ash content. In yet further embodiments, post-grinding modification decreases the concentration of total dissolved solids. In further implementations, post-grinding modification comprises adjusting the pH and or increase the surface area of the particles In further aspects, post-grinding processing seeks to further reduce moisture content of the microbechar.

In certain aspects, the modification of the microbechar is by way of the addition of a chemical additive to the microbechar. According to certain implementations of these embodiments, the chemical additive may be: aromatic compounds, alcohols, salts (e.g., ammonium persulfate), surfactants (e.g., Avenel), oils/fats/fatty acids/lipids, water (e.g., steam) ionic liquids, hydrogenation, chemical hydrolysis, enzymatic hydrolysis, alkali solvents (e.g., sodium hydroxide, ammonia, carbon dioxide), carbon dioxide, chlorine gasses, sulfur gasses, nitrogen gasses, and oxygen gasses.

In certain implementations, post-milling microbechar surface modifications are made through a hydrogen peroxide treatment. In exemplary embodiments, following milling, the microbechar is separated through freeze drying and analyzed for purity. Following separation, the microbechar is further functionalized with a 30% (w/w) hydrogen peroxide solution and refluxed. In certain embodiment reflux occurs for about 24 hours at about 60° C. Following reflux, the excess hydrogen peroxide is removed. In exemplary embodiments, hydrogen peroxide is removed by dialysis against DI water in tubing until no remaining peroxide is detected. The final functionalized powder can then be freeze dried again and analyzed by SEM EDS to help gauge the extent of surface modification.

According to further aspects, the modification of the microbechar comprises drying the microbechar. According to these embodiments, this dry step is carried out by way of a method selected from a list consisting of: drum filtration, dead-end filtration, microfiltration, ultra-filtration, pressure filtration, vacuum filtration, tangential flow filtration, diatomaceous earth filtration, membrane filtration, magnetic separation, forward osmosis, electrofloation, roller press, belt harvesters, capillary extraction, simple heating/evaporation, hydrocyclone, crossflow, assisted separation (magnetic, electric, dielectric, acoustic), granular bed filters, precoat filters, disc stack centrifugation, cross flow filtration, decanter centrifugation, and organic flocculation. In certain embodiments, the drying step is performed through a combination of the foregoing.

In certain aspects, the post-milling drying step is performed until a predetermined threshold of moisture reduction has been met. In certain exemplary embodiments, the drying step is performed until the moisture content of the microbechar is reduced to below about 8%.

This drying removes anywhere between 30 and 99% of all solution from the biomass This drying may or may not be included in this process Any/all of the above or any combination of any of the above In certain embodiments, the method further includes the step of washing the microbial biomass prior to the thermal processing step.

According to certain aspects, the disclosed methods are carried out according to the following steps. In a first step, biomass, either wet or dry, is added to an aqueous solution of calcium salt, first ion source, or precipitate-precursor. In various implementations, calcium chloride is the calcium source. The concentration of the calcium salt in the aqueous suspension is about 0.75 to 30% by weight, about 1 to 20% by weight, or about 1.5 to 10% by weight.

In a further step the biomass is suspended in the solution. The concentration of biomass suspended in the aqueous solution of calcium salt is within a range of about 0.1 to 40% by weight in terms of solid content, or alternatively a range of about 2 to 20% by weight. The suspension is prepared in a range where the temperature of the aqueous suspension is about 0 to 40° C., or about 10 to 35° C.

In a further optional step, the mixture is sheared or sonicated to disrupt the cell membranes. This step may also accelerate the absorption of calcium salt by the cells.

In another step, the mixture is stirred at 0-40° C. for 0-20 hours, or 1-20 hours, or 0.5-2 hours.

In another step, an aqueous solution of phosphate, second ion source, or counter-precipitate-precursor ion is added to the mixture. The phosphate, second ion source, or counter-precipitate-precursor ion may also be in a solid form. In certain implementations, trisodium phosphate is used. The phosphate concentration may be about 1.25 to 50% by weight, about 2 to 30%, or about 2.5 to 20%, calculated based on the final volume of the biomass mixture.

In a next optional step, the mixture is stirred at 0-40° C. for 1-20 hrs. In certain implementations, the mixture is stirred at 0 to 35° C. for 0 to 20 hours or in some implementations for about 0.5 to 2 hours.

In a next step, precipitates and biomass are filtered out. The precipitates and biomass can be filtered from the liquids, using various filtration methods, for example gravity sedimentation, centrifugal sedimentation, filter press, and the like. In various implementations a filter press is used.

In another step, the solids are then dried and charred.

In a further step, the char is acid washed to remove ash. In certain implementations, the acid is used to dissolve various mineral components. In various implementations, the acid is hydrochloric acid. In certain implementations, the acid has a pH of about −1.0 and 6 or about 0.1 to 3.0.

EXPERIMENTAL EXAMPLES

The following examples are put forth so as to provide those of ordinary skill in the art with a complete disclosure and description of how the articles, devices and/or methods claimed herein are made and evaluated, and are intended to be purely exemplary of the invention and are not intended to limit the scope of what the inventors regard as their invention. However, those of skill in the art should, in light of the present disclosure, appreciate that many changes can be made in the specific embodiments which are disclosed and still obtain a like or similar result without departing from the spirit and scope of the invention.

Example 1

In this example, 3.46 g of calcium chloride was added to 100.97 g of DI water. Next, 8.28 g of yeast was added to the aqueous solution of calcium chloride, resulting in a biomass suspension. The mixture was sheared with a shear mixer at 2000 RPM with 1.5 inch blade for 3 mins and stirred with a magnetic stir plate at 100° F.

Next, 7.38 g of trisodium phosphate is added to 149.81 g of DI water. The aqueous solution of trisodium phosphate was then added all at once to the biomass mixture. The final resulting mixture was stirred for 1.5 hr at RT and centrifuged at 2500 RPM for 5 mins. The supernatant was discarded and the solid was dried at 160° F. All samples were processed with a SPIRAJOULE® SPJ HT heated screw pyrolyzer at a temperature of 565° C. for 20 minutes within a Nitrogen gas environment.

Example 2

In this example, 2.99 g of calcium chloride is added to 99.50 g of DI water. Next, 8.11 g of spirulina was added to the aqueous solution of calcium chloride, resulting in a biomass suspension. The mixture was sheared with a shear mixer at 2000 RPM with 1.5 inch blade for 2 mins and stirred with a magnetic stir plate at 150° F.

Next, 7.49 g of trisodium phosphate is added to 149.52 g of DI water. The aqueous solution of trisodium phosphate was added all at once to the biomass mixture. The final resulting mixture was stirred for 2 hr at RT and centrifuged at 2500 RPM for 5 mins. The supernatant was discarded and the solid was dried at 160° F. All samples were processed with a SPIRAJOULE® SPJ HT heated screw pyrolyzer at a temperature of 565° C. for 20 minutes within a Nitrogen gas environment.

Example 3

In one example, salts were removed form biomass prior to charring causing biomass to melt together. The presence of salts on the biomass pre-charring allows for (i) particles to remain distinct and (ii) pores to form in the biomass.

Figure 1B:
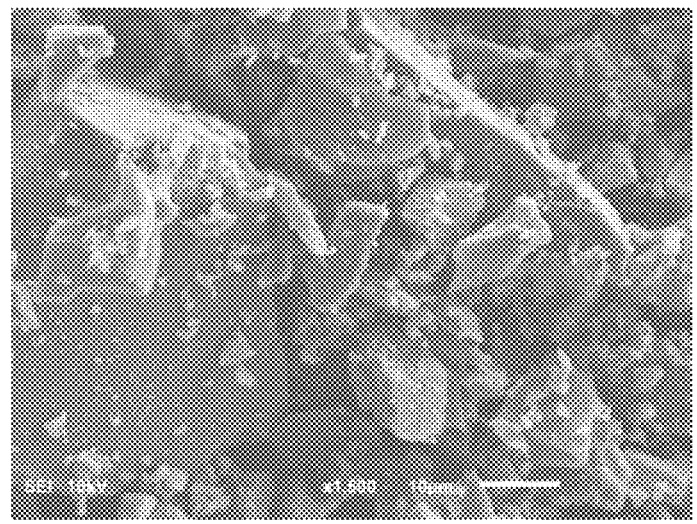
FIG. 1B is an SEM image of charred Spriulina biomass (Arthrospira) that was washed of all salts, prior to charring, according to one embodiment.
Figure 1C:
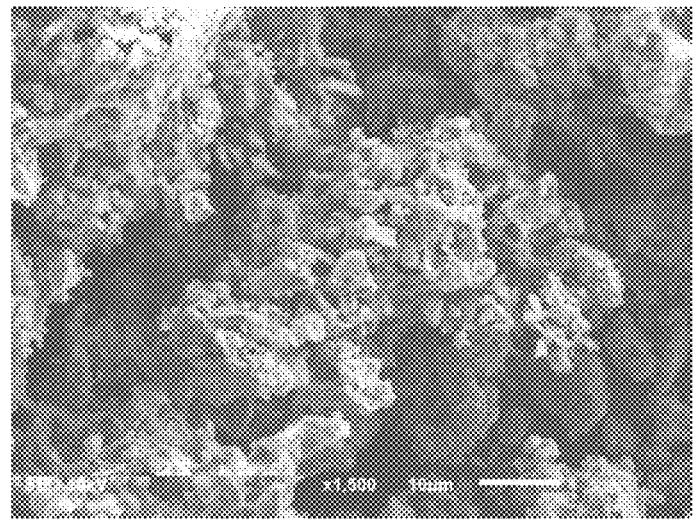
FIG. 1C is SEM image of charred Spriulina biomass (Arthrospira) where the cleaned and unsalted biomass was retreated with a soluble anion/cation mixture prior to charring, according to one embodiment.

FIG. 1A shows the biomass that had been treated with the soluble anion/cation mixtures and then charred. FIG. 1B shows the biomass in which the salts were removed prior to charring, via acid washing, and then charred. In FIG. 1B, the biomass had amorphous features. FIG. 1C shows the biomass of FIG. 1B that has been 'rescued', that is the biomass from FIG. 1B was re-treated with the soluble anion/cation mixtures and the re-treated material was then charred. In FIG. 1C a multitude of pores can be seen.

Example 4

Figure 2A:
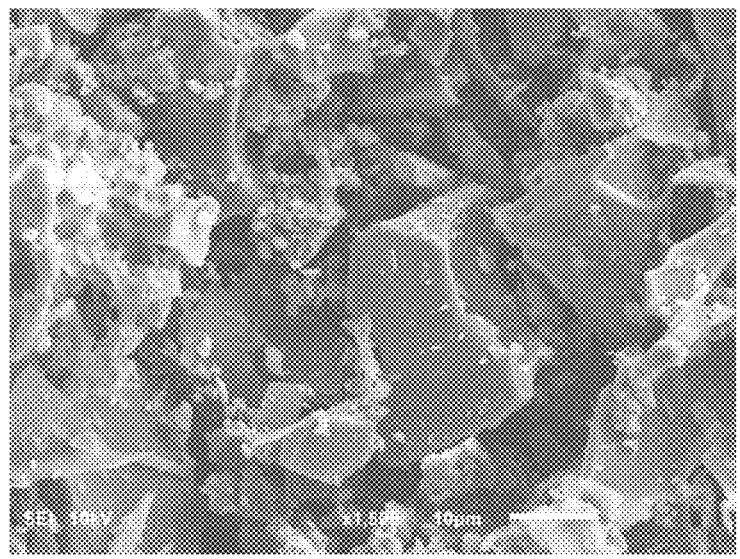
FIG. 2A is an image of pure and untreated charred Spriulina biomass (Arthrospira), according to one embodiment.
Figure 2B:
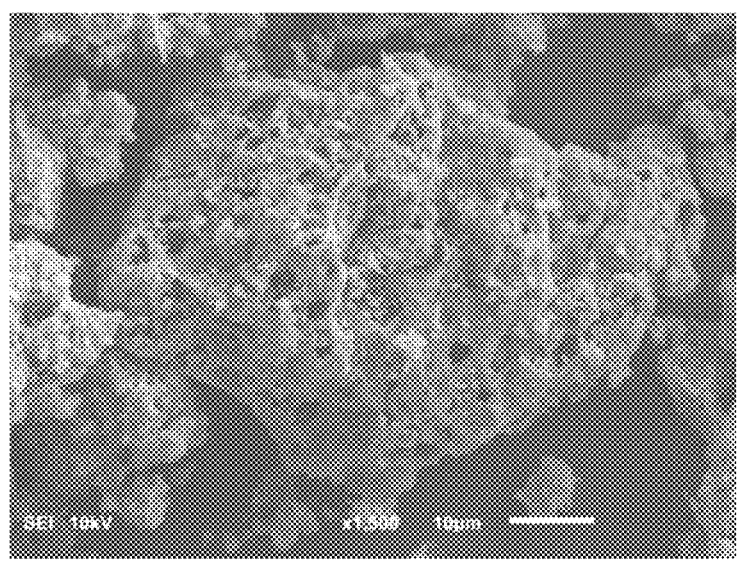
FIG. 2B is an SEM image of pure untreated charred Spriulina biomass (Arthrospira)that was treated with a soluble anion/cation mixture prior to charring, according to one embodiment.

In this example, the biomass used was photosynthetic microbes sold in stores as whole cell cyanobacteria, washed of any salts (Earthrise, spirulina (photosynthetic prokaryote), Grocery store spirulina). FIG. 2A shows charred biomass that had not received any treatment. FIG. 2B shows biomass that was treated with a soluble anion/cation mixture and then charred. In FIG. 2B distinct particles with a heavily porous surface are shown.

Example 5

Figure 3A:
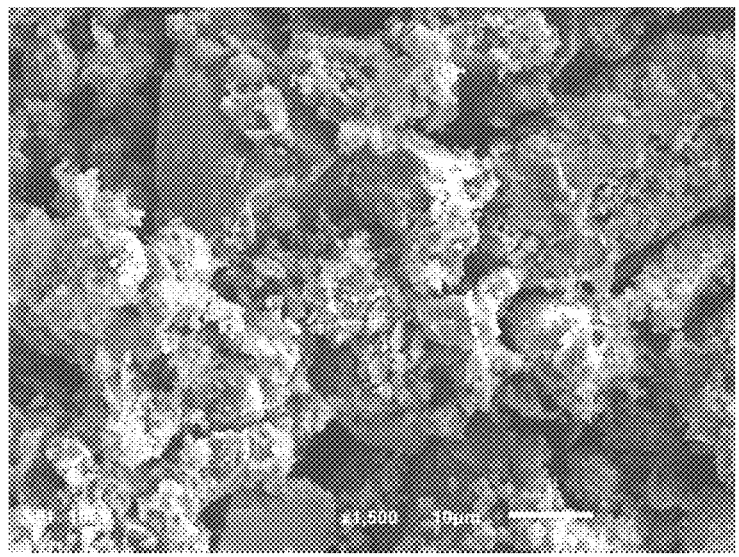
FIG. 3A is an SEM image of untreated charred Yeast (Saccharomyces, Candida, or other yeast genus) biomass, according to one embodiment.
Figure 3B:
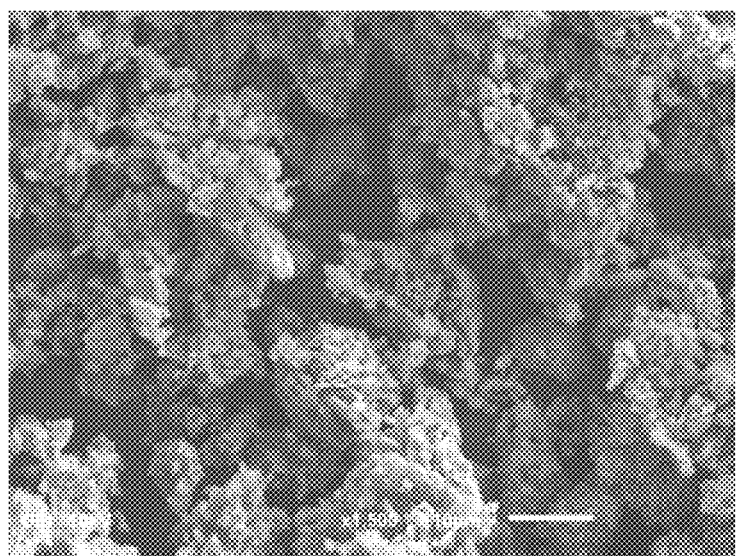
FIG. 3B is an SEM image of charred Saccharomyces/Candida/or other yeast genus) biomass that was treated with a soluble anion/cation mixture prior to charring, according to one embodiment.
Figure 7A:
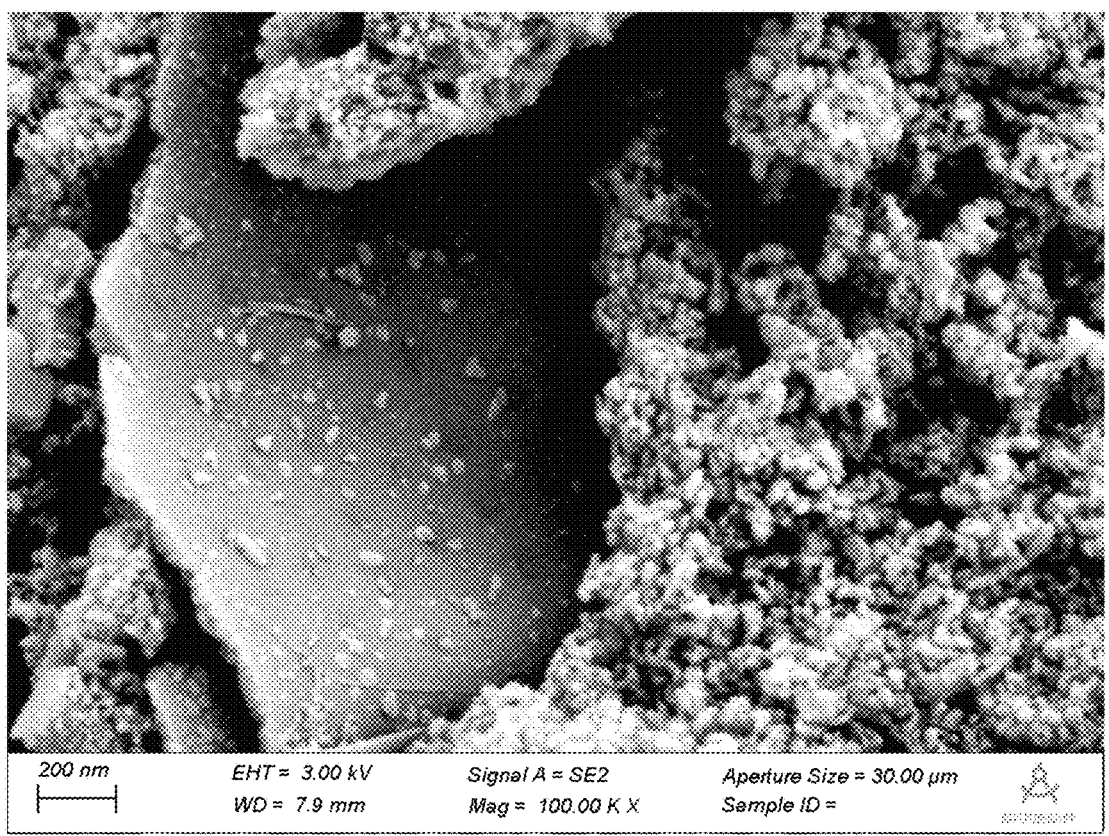
FIG. 7A is a microscopic image of charred biomass that was treated with a soluble anion/cation mixture prior to charring, according to one embodiment.
Figure 7B:
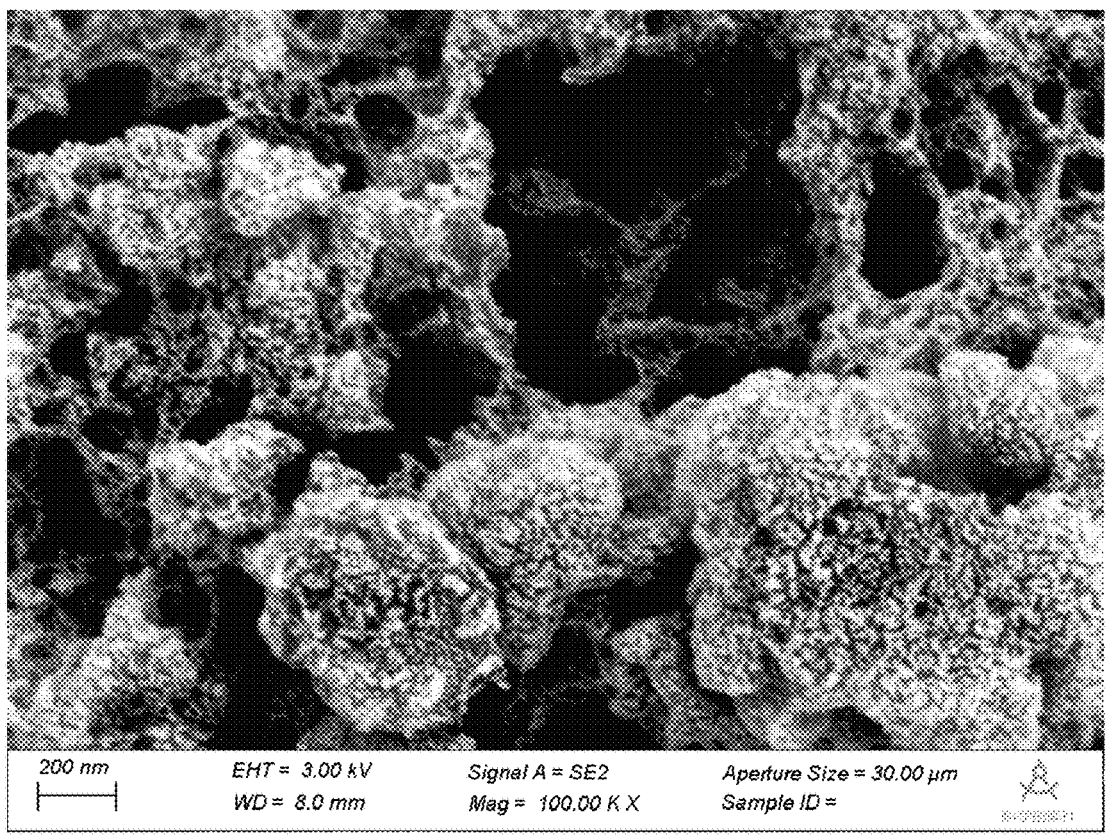
FIG. 7B is a microscopic image of salted and charred biomass with salt removed via an post charring acid wash, according to one embodiment.

In this example, the biomass used was whole-cell yeast from a fermenter (Researcher from UC-Anschutz, yeast (heterotrophic eukaryote), yeast). FIG. 3A shows charred biomass that had not received any treatment. FIG. 3B shows biomass that was treated with a soluble anion/cation mixture and then charred.

Example 6

In this example, salting of biomass prior to charring generated a char that has high flowability/pourability characteristics. A summary of the results of Example 4 is shown in Table 1. FIG. 4A shows Spirulina biomass that was washed of any salts and then charred. In FIG. 4A the biomass mushroomed into a solid—non-flowable mass, unlike its original state. FIG. 4B shows spirulina biomass that was washed and then salted with a sequential soluble anion/cation mixture, and then charred. In the example of FIG. 4B the charred biomass remained as a flowable mass that had not distorted in form.

FIG. 5A shows unsalted yeast biomass that was charred and formed into a hard mass. As can be seen in FIG. 5A the charred biomass hardened into a puck in the center of the container, distorted into a form different from its original state. FIG. 5B shows yeast biomass that was treated with a soluble anion/cation mixture prior to charring. The salted and charred biomass filled the container and was not charred into a hard mass, and remained flowable, post charring.

Example 7

As shown in Tables 2-4, salting biomass prior to charring and acid washing post charring was shown to substantially increase the jetness value. Also, salting biomass prior to charring substantially increases the flowability of the charred biomass, represented by the charred biomass not sticking to itself and flowing freely.

Example 8

In FIG. 6A an example of salt crystals formed on salted-charred biomass is shown. In FIG. 6B the salt was removed via acid treatment from the salted-charred biomass, thus, revealing the highly porous nature of the resultant charred biomass.

Imaging

FIGS. 1-3: Scanning electron microscopic images were acquired for all the samples post TGA. Images were acquired using the Jeol/EQ InTouchscope. 5-10 mg of sample was dusted onto a double sided carbon fixed onto an SEM stub. Samples were sputter coated with gold and palladium prior to reduce any charging during imaging. Images were acquired at 150×, 500× and 1500× magnification.

FIGS. 4 & 5: Optical images of samples were acquired post TGA and were taken in the 5ml volume crucibles that were used to char the material in question within the TGA. Images were taken on cellular phones.

FIG. 6: Scanning electron microscopic images were acquired for all the samples post TGA. Image capture occurred on a Phenom Prox Desktop scanning electron micrograph equipped with energy dispersive X-ray spectroscopy. 5-10 mg of sample was dusted onto a double-sided carbon fixed onto an SEM stub. Samples were sputter coated with gold and palladium prior to reduce any charging during imaging. Images have a 100,000× magnification.

Although the disclosure has been described with reference to preferred embodiments, persons skilled in the art will recognize that changes may be made in form and detail without departing from the spirit and scope of the disclosed apparatus, systems and methods.

What is claimed is:

1. A method for producing a carbon black pigment from a microbial biomass comprising:
providing a microbial biomass solution comprising a plurality microbial cells in an aqueous solvent;
nucleating the plurality of microbial cells by adding a first soluble ion to the microbial biomass solution;
initiating crystal formation in and/or on the plurality of microbial cells by adding a second soluble ion to the microbial biomass solution, forming a plurality of crystal encrusted microbial cells, wherein the charge of the first soluble ion is the opposite of the charge of the second soluble ion and wherein the crystals are formed from precipitation of the first and second ions;
performing thermal processing of the plurality of crystal encrusted microbial cells to form a charred biomass; and
washing the charred biomass to form a microbechar.

2. The method of claim 1, wherein the first ion is an anion and the second ion is a cation.

3. The method of claim 1, wherein the first ion is a cation and the second ion is an anion.

4. The method of claim 3, wherein the cation is calcium and the anion phosphate.

5. The method of claim 1, wherein first ion and second ion are present at a stoichiometric ratio.

6. The method of claim 1, wherein the nucleating step further comprises performing a nucleation incubation by incubating the first ion with plurality of microbial cells for a period of from about 5 minutes to about two hours.

7. The method of claim 6, wherein the incubation step further comprises heating the microbial biomass solution to a temperature from about 32° C. to about 65° C.

8. The method of claim 6, further wherein the incubation step further comprises agitating the microbial biomass solution.

9. The method of claim 8, wherein the agitating step is performed through sheer mixing the microbial biomass solution at about 2000 RPM for about two minutes.

10. The method of claim 1, wherein the crystal formation step further comprises crystallization incubation by incubating the nucleated microbial biomass solution with the second ion for a period of from about 5 minutes to about two hours.

11. The method of claim 1, wherein the plurality of crystal encrusted microbes has cell surface crystal formation and/or wherein the plurality of crystal encrusted microbes has cell intracellular crystal formation.

12. The method of claim 1, wherein the microbial biomass is comprised of a plurality of prokaryotic cells, wherein the average cell size of the prokaryotic cells is below about 50 μm.

13. The method of claim 1, wherein the microbial biomass is dried at temperature of from about 30 ° C. and about 300 ° C., prior to the thermal processing step and wherein the microbial biomass is dried until moisture content is reduced to below about 15%.

14. The method of claim 1, wherein the thermal processing steps is performed until the charred biomass is comprised of fixed carbon of from about 20% to about 70%.

15. The method of claim 1, wherein the thermal processing step is performed until the concentration of oxygen is from about 10 and 15%.

16. The method of claim 1, wherein the wash of the charred biomass is an acid wash wherein the acid wash comprises reducing the pH of the charred biomass to below about 2 for a time interval from about 1 minute to about 1 hour.

17. The method of claim 16, further comprising washing the charred biomass in water following the acid wash and wherein the acid wash and subsequent water wash produces a porous microbechar.

18. The method of claim 1, further comprising a grinding step following the washing of the microbechar, wherein the grinding step is performed until the average particle size diameter of the milled microbechar is less than about 10 microns.

19. The method of claim 1, wherein the carbon black pigment produced has increased flowability relative to microbial biomass with comparable thermal processing without crystal formation.

20. The method of claim 1, wherein the carbon black pigment produced has increased porosity relative to microbial biomass with comparable thermal processing without crystal formation and/or the carbon black pigment produced has increased jetness relative to microbial biomass with comparable thermal processing without crystal formation.

21. A method for producing an engineered carbon black pigment from a microbial biomass comprising:
performing thermal processing of the microbial biomass, wherein the microbial biomass comprises a plurality of crystal encrusted microbial cells to form a charred biomass; and
washing of the charred biomass is an acid wash, wherein the washing step comprises reducing the pH of the charred biomass to below about 2 for a time interval from about 1 minute to about 1 hour to form a microbechar.

* * * * *